(12) United States Patent
Sinha et al.

(10) Patent No.: US 9,176,250 B2
(45) Date of Patent: Nov. 3, 2015

(54) ESTIMATION OF DEPLETION OR INJECTION INDUCED RESERVOIR STRESSES USING TIME-LAPSE SONIC DATA IN CASED HOLES

(75) Inventors: Bikash K. Sinha, Cambridge, MA (US); Ergun Simsek, Chevy Chase, MD (US)

(73) Assignee: Schlumberger Technology Corporation, Sugar Land, TX (US)

( * ) Notice: Subject to any disclaimer, the term of this patent is extended or adjusted under 35 U.S.C. 154(b) by 862 days.

(21) Appl. No.: 13/248,891

(22) Filed: Sep. 29, 2011

(65) Prior Publication Data

US 2013/0081804 A1 Apr. 4, 2013

(51) Int. Cl.
*E21B 47/00* (2012.01)
*G01V 1/50* (2006.01)
*G01V 1/42* (2006.01)
*E21B 47/10* (2012.01)

(52) U.S. Cl.
CPC ............... *G01V 1/42* (2013.01); *E21B 47/101* (2013.01)

(58) Field of Classification Search
CPC ........... E21B 49/006; G01V 1/50; G01V 1/48
USPC ........... 166/250.01, 250.1; 367/25, 31; 702/6, 702/11
See application file for complete search history.

(56) References Cited

U.S. PATENT DOCUMENTS

| 6,351,991 | B1 | 3/2002 | Sinha |
| 7,463,550 | B2 | 12/2008 | Sinha et al. |
| 2009/0145600 | A1* | 6/2009 | Wu et al. .................. 166/250.02 |
| 2010/0020642 | A1 | 1/2010 | Sinha |
| 2011/0077920 | A1 | 3/2011 | Lei et al. |
| 2011/0134720 | A1 | 6/2011 | Bratton et al. |
| 2012/0061077 | A1* | 3/2012 | Fraim et al. .................. 166/249 |

OTHER PUBLICATIONS

International Search Report and Written Opinion of PCT Application No. PCT/US2012/054597 dated Feb. 25, 2013: pp. 1-9.
Norris et al., "Acoustoelasticity of solid/fluid composite systems," Geophys. J. Int., 1994, vol. 118: pp. 439-446.
Pistre et al., "A Modular Wireline Sonic Tool for Measurements of 3D (Azimuthal, Radial, and Axial) Formation Acoustic Properties," SPWLA 46th Annual Logging Symposium, Jun. 2005: pp. 1-13.
Sinha, "Elastic Waves in Crystals Under a Bias," Ferroelectrics, 1982, vol. 41: pp. 61-73.

* cited by examiner

*Primary Examiner* — Catherine Loikith
(74) *Attorney, Agent, or Firm* — Jakub Michna

(57) ABSTRACT

An apparatus and a method for recovering hydrocarbons from a subterranean formation including collecting baseline and subsequent sonic data. Either open or cased hole Stoneley and cross dipole dispersions are calculated using the baseline and subsequent sonic data, the minimum and maximum horizontal stress magnitudes are calculated using the calculating dispersions, a pressure is calculated and hydrocarbons are recovered.

22 Claims, 10 Drawing Sheets

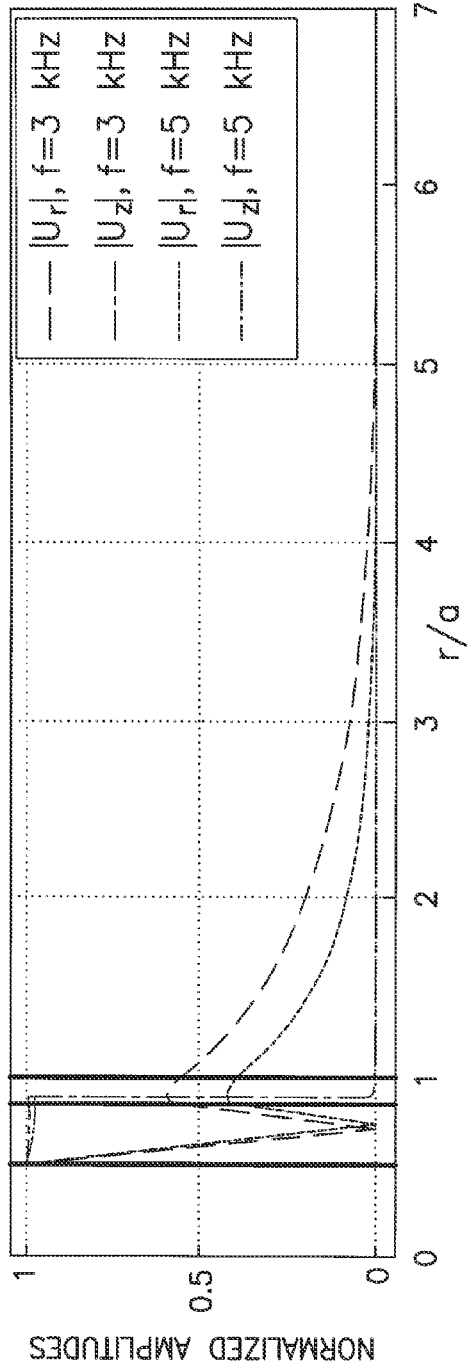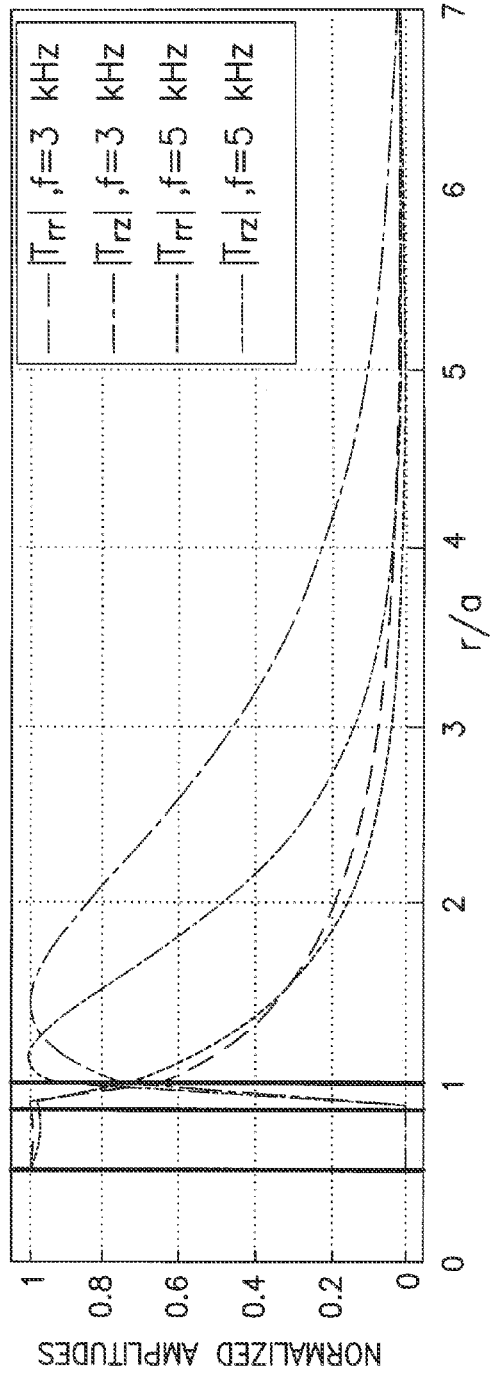

ESTIMATION OF DEPLETION OR INJECTION INDUCED RESERVOIR STRESSES USING TIME-LAPSE SONIC DATA IN CASED HOLES

FIELD

Embodiments of this application relate to estimating changes in subterranean formation stresses caused by reservoir depletion or injection using time-lapse borehole sonic data.

BACKGROUND

Mechanical disturbances can be used to generate elastic waves in earth formations surrounding a borehole, and the properties of these waves can be measured to obtain important information about the formations through which the waves have propagated. Parameters of compressional, shear and Stoneley waves, such as their velocity (or its reciprocal, slowness) in the formation and in the borehole, are indicators of formation characteristics that help in evaluation of the location and/or producibility of hydrocarbon resources. Recent studies of wave propagation in prestressed materials indicate that one may invert measured compressional and shear slowness data to estimate formation stress parameters.

A logging device that has been used to obtain and analyze sonic logging measurements of formations surrounding an earth borehole is a SONIC SCANNER™ such as a general type described in Pistre et al., "A modular wireline sonic tool for measurements of 3D (azimuthal, radial, and axial) formation acoustic properties, by Pistre, V., Kinoshita, T., Endo, T., Schilling, K., Pabon, J., Sinha, B., Plona, T., Ikegami, T., and Johnson, D.", Proceedings of the 46$^{th}$ Annual Logging Symposium, Society of Professional Well Log Analysts, Paper P, 2005. The SONIC SCANNER™ allows one to present compressional slowness, $\Delta t_c$, shear slowness, $\Delta t_s$, and Stoneley slowness, $\Delta t_{st}$, each as a function of depth, z. [Slowness is the reciprocal of velocity and corresponds to the interval transit time typically measured by sonic logging tools.]

An acoustic source in a fluid-filled borehole generates headwaves as well as relatively stronger borehole-guided modes. A standard sonic measurement system consists of placing a piezoelectric source and an array of hydrophone receivers inside a fluid-filled borehole. The piezoelectric source is configured in the form of either a monopole or a dipole source. The source bandwidth typically ranges from a 0.5 to 20 kHz. A monopole source generates primarily the lowest-order axisymmetric mode, also referred to as the Stoneley mode, together with compressional and shear headwaves. In contrast, a dipole source primarily excites the lowest-order flexural borehole mode together with compressional and shear headwaves. The headwaves are caused by the coupling of the transmitted acoustic energy to plane waves in the formation that propagate along the borehole axis. An incident compressional wave in the borehole fluid produces critically refracted compressional waves in the formation. Those refracted along the borehole surface are known as compressional headwaves. The critical incidence angle $\theta_i = \sin_{-1}(V_f/V_c)$, where $V_f$ is the compressional wave speed in the borehole fluid; and $V_c$ is the compressional wave speed in the formation. As the compressional headwave travels along the interface, it radiates energy back into the fluid that can be detected by hydrophone receivers placed in the fluid-filled borehole. In fast formations, the shear headwave can be similarly excited by a compressional wave at the critical incidence angle $\theta_i = \sin^{-1}(V_f/V_s)$, where $V_s$ is the shear wave speed in the formation. It is also worth noting that headwaves are excited only when the wavelength of the incident wave is smaller than the borehole diameter so that the boundary can be effectively treated as a planar interface. In a homogeneous and isotropic model of fast formations, as above noted, compressional and shear headwaves can be generated by a monopole source placed in a fluid-filled borehole for determining the formation compressional and shear wave speeds. It is known that refracted shear headwaves cannot be detected in slow formations (where the shear wave velocity is less than the borehole-fluid compressional velocity) with receivers placed in the borehole fluid. In slow formations, formation shear velocities are obtained from the low-frequency asymptote of flexural dispersion. There are processing techniques for the estimation of formation shear velocities in either fast or slow formations from an array of recorded dipole waveforms.

Borehole sonic data after reservoir depletion or injection is, generally, acquired in a cased hole. However, processing of sonic data in a cased hole for estimating the three shear moduli is more challenging. Among other things, quality of bond between the casing and cement is an important factor in the processing and interpretation of sonic data.

SUMMARY

Embodiments relate to apparatus and a method for recovering hydrocarbons from a subterranean formation including collecting baseline and subsequent sonic data, calculating cased hole Stoneley and cross dipole dispersions using the baseline and subsequent sonic data, estimating the minimum and maximum horizontal stress magnitude using the calculating dispersions, calculating a pressure, and recovering hydrocarbons.

FIGURES

FIG. 3 is a series of plots of the normalized amplitude as a function of radial variation at 3 and 5 kHz.

DETAILED DESCRIPTION

Figure 1:
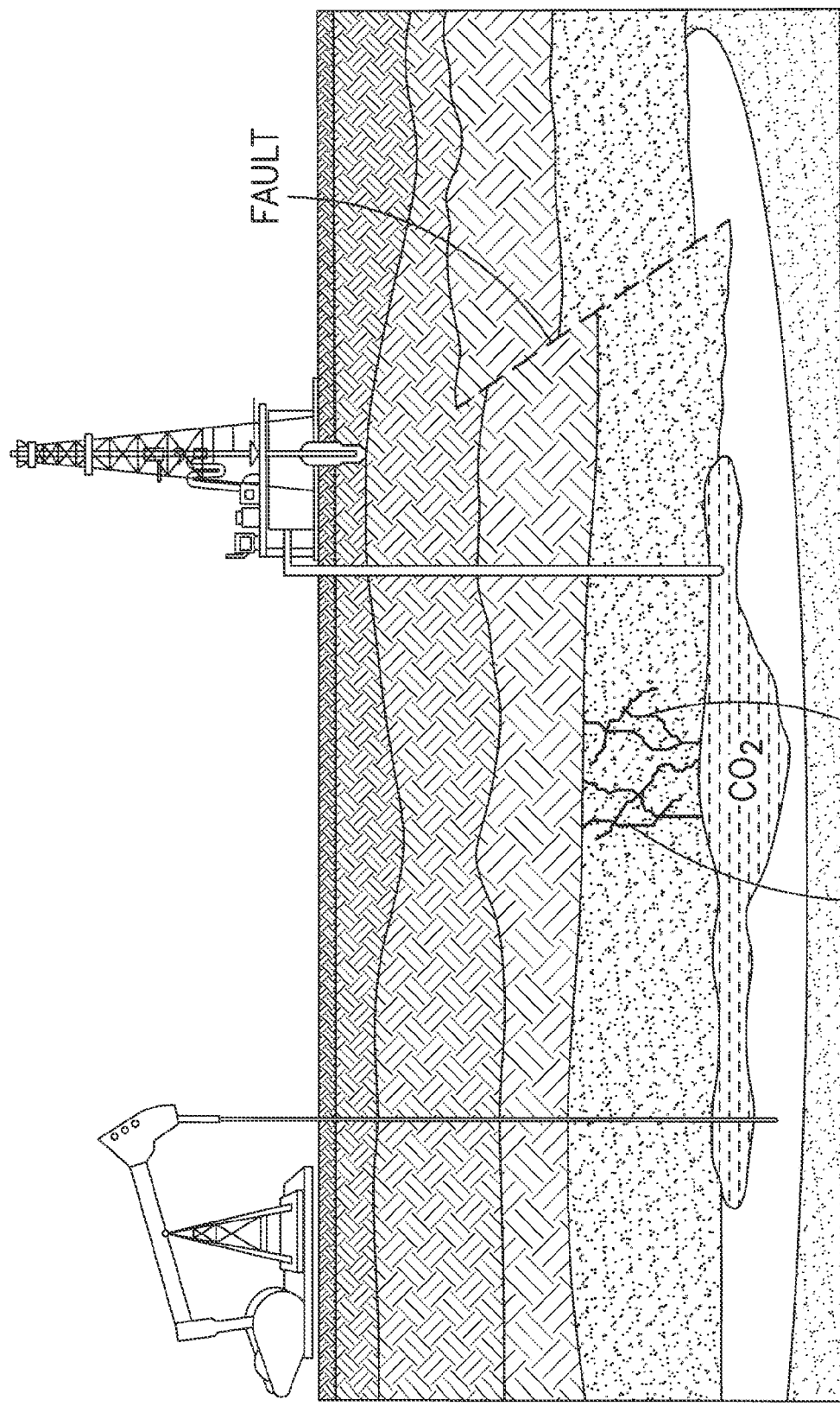
FIG. 1 is a schematic diagram of a subterranean formation during or after carbon dioxide and/or water injection in a tertiary recovery project.

Reservoir depletion and subsequent fluid (water and carbon dioxide) injection for enhanced oil recovery cause changes in the reservoir pressure and formation stresses. Large stress changes can lead to activation of pre-existing faults and cap rock fractures that can lead to unwanted $CO_2$ leakage. It is important to monitor reservoir stresses as a function of changes in reservoir pressure to avoid reactivation of an existing fault or introduction of unwanted fractures in the cap rock that would result in $CO_2$ leakage. Time-lapse seismic surveys can detect impedance changes on the order of 3 to 9 percent in $CO_2$ saturated rocks and are indicators of qualitative changes in the reservoir pressure and saturation. A technique for detecting small sonic velocity changes that can be related to changes in in-situ stresses and fluid mobility caused by either reservoir depletion or injection is discussed herein. Reliable estimates of these changes help reservoir managers maintain reservoir integrity and tailor sequestration of injected carbon dioxide.

Sonic velocities in formations change as a function of rock lithology/mineralogy, porosity, clay content, fluid saturation, stresses, and temperature. To estimate changes in the formation stress magnitudes from measured changes in sonic velocities, it is necessary to select a depth interval with a reasonably uniform lithology, clay content, saturation, and temperature so that the measured changes in velocities can be largely related to corresponding changes in formation stress magnitudes. Any change in porosity caused by normal compaction in the chosen depth interval is accounted for in the inversion model by a corresponding change in the formation effective elastic moduli and density. Assuming that the measured changes in sonic velocities are largely caused by changes in stress magnitudes, it is possible to invert borehole sonic velocities for the estimation of changes in formation stress magnitudes.

It has been demonstrated that differences in shear moduli are related to differences in principal stresses in a homogeneously stressed rock. There are two independent difference equations relating the three shear moduli $C_{44}$, $C_{55}$, and $C_{66}$, and three unknowns: the maximum and minimum horizontal stresses, and an acoustoelastic coefficient. Consequently, we have two independent equations relating three unknowns. However, we can solve for the maximum horizontal stress magnitude and an acoustoelastic coefficient when a Mechanical Earth Model provides the overburden stress, pore pressure, and minimum horizontal stress as a function of depth. The minimum horizontal stress can be estimated from extended leak-off or mini-frac tests.

This algorithm for the estimation of $S_{Hmax}$ using the three shear moduli assumes that differences in the three shear moduli are primarily caused by differences in the three principal stresses—the overburden, maximum and minimum horizontal stresses. While this assumption is largely valid in a sand reservoir with moderate fluid permeability, it is possible to correct for the fluid permeability or mobility induced bias in the measured Stoneley shear modulus $C_{66}$ in the borehole cross-sectional plane. The presence of fluid mobility in the absence of any stress effects increases the Stoneley slowness in the low and intermediate frequency band of 1 to 3 kHz. This is associated with a decrease in the Stoneley shear modulus $C_{66}$ that can be estimated from a forward model based on a low-frequency approximation of the Biot model. Generally, a fluid mobility of 100 to 1000 md/cp can cause a reduction of the shear modulus $C_{66}$ by about 5 to 10%. Therefore, we are required to increase the measured value of $C_{66}$ by this amount before inputting $C_{66}$ into the stress magnitude estimation algorithm. We suggest that we calculate fluid mobility induced effects on $C_{66}$ (in the absence of stresses) using an independent estimate of the fluid permeability/mobility from a MDT pretest, NMR or core permeability. When fluid mobility from an independent source is not known, we recommend that the stress magnitude estimation algorithm should be run for at least two additional values of $C_{66}'$ that could describe an upper-bound and lower-bound on $C_{66}'$ in view of possible bias in the data caused by the fluid permeability.

Similarly, we can compensate for the bias on the shear modulus $C_{66}'$ caused by the intrinsic (shale) TI-anisotropy in the estimation of formation stress magnitudes provided we have estimated this structural anisotropy from core samples in the presence of confining pressure at the depth of interest. Generally, $C_{66}$ is larger than $C_{44}$ or $C_{55}$ in a horizontally-layered TI-formation. Consequently, the measured $C_{66}$ needs to be reduced by an amount that has been introduced because of structural effects. In the absence of any real core data, we can run the stress-magnitude algorithm using an upper-bound and lower-bound for the $C_{66}$ modulus that would cover possible effects of structural or intrinsic anisotropy. This procedure would enable putting a reasonable bound on the estimated stress magnitudes that accounts for the structural anisotropy bias on the measured shear moduli.

FIG. 1 shows a schematic diagram of $CO_2$ and water injection to enhance hydrocarbon production in a tertiary recovery project. It is important to monitor changes in the reservoir pressure and stresses to reduce chances of $CO_2$ leakage through cap rock fracture or re-activation of any pre-existing fault. Sonic data in cased holes acquired before and after reservoir depletion or injection exhibits changes on the order of 2 to 6 percent in the compressional velocity together with borehole Stoneley and dipole flexural dispersions. This procedure described herein estimates time-lapse changes in the three shear moduli using sonic data. This procedure is based on analyzing sensitivity of measured borehole dispersions to various formation and borehole fluid parameters. Shear moduli are then estimated from the measured borehole dispersions. These far-field shear moduli can be transformed into corresponding changes in the formation effective stresses. However, an independent estimate of any increase in fluid mobility possibly caused by $CO_2$ induced oil swelling is desirable. In the absence of any such estimate of fluid mobility change, we can estimate an upper bound to the difference between the overburden and horizontal stresses as a parameter in controlling the fracture pressure.

Reservoir depletion or fluid injection for enhanced recovery can lead to two types of structural failure. First, if the present reservoir stresses together with pore pressure cause the breakdown pressure $P_B$ to exceed a threshold, cap rock fractures are initiated and reservoir integrity is damaged. The breakdown pressure is given by the following equation $$P_B = 3S_h - S_H - \alpha P_P + T_S, \quad (1)$$

where $S_h$ and $S_H$ are the minimum and maximum horizontal stresses, $\alpha$ is the Biot parameter, $P_P$ is the pore pressure, and $T_S$ is the rock tensile strength.

Second, if the pore pressure $P_P$ exceeds a threshold given by the Coulomb criterion for the initiation of slip along a pre-existing fault, a reactivation of such faults would also cause reservoir damage. To mitigate risk of such slippage, the reservoir pressure must be maintained below a threshold given by $$P_P \leq \sigma_n - \tau/\mu_f + C/\mu_f, \quad (2)$$

$$\sigma_n = S_H \cos^2 \theta + S_V \sin^2 \theta, \quad (3)$$

$$\tau = 0.5(S_V - S_H) \sin 2\theta, \quad (4)$$

where $\theta_n$ and $\tau$ are the normal and shear stresses acting on a fault making an angle $\theta$ with the horizontal; $S_V$ and $S_H$ are the formation overburden and horizontal stresses; C is the cohesion strength and $\mu_f$ is the coefficient of internal friction.

The procedure for the estimation of changes in the formation effective stresses includes the following.

1. Before production (or injection), estimate the overburden and minimum horizontal stresses together with pore pressure.
2. Measure the far-field compressional slowness and the borehole Stoneley and cross-dipole dispersions using sonic data in a cased hole or open hole in a reservoir interval. This constitutes a baseline survey.
3. Estimate the far-field shear moduli using borehole dispersions.
4. Calculate an acoustoelastic coefficient based on a nonlinear continuum mechanics model.
5. After production (or injection), measure the far-field compressional slowness and borehole Stoneley and cross-dipole flexural dispersions in the cased hole. This is referred to as a monitor survey.
6. Estimate the far-field three shear moduli using sonic data acquired in step 5.
7. Estimate changes in the far-field formation effective stresses using differences in the shear moduli and acoustoelastic coefficient calculated before production (or injection) in step 4.

Inversion of borehole sonic data for formation stress parameters assumes that the measured changes in plane wave velocities in the far-field are caused primarily by corresponding changes in stresses. Note that changes in the elastic moduli are determined either from measured plane wave velocities or inversion of borehole dispersions.

Generally, embodiments of this relate to a technique for estimating changes in formation stresses caused by reservoir depletion or injection using time-lapse borehole sonic data. A baseline survey consists of sonic data acquired in an open or cased hole together with estimates of reservoir pressure, overburden and minimum horizontal stresses. Subsequently, a monitor survey would comprise sonic data acquired in an observation well. Sonic data acquired before and after depletion or injection is processed to obtain the borehole Stoneley and cross-dipole dispersions. An inversion algorithm inverts the measured Stoneley dispersion to estimate the far-field shear modulus C66 in the borehole cross-sectional plane. The two cross-line flexural dispersions yield the two shear moduli $C_{44}$ and $C_{55}$ in the two orthogonal planes containing the borehole axis. These two shear moduli are obtained directly from the low-frequency asymptotes of the two flexural dispersions. Differences in the three shear moduli from the baseline survey yield the maximum horizontal stress magnitude and an acoustoelastic coefficient using estimates of the pore pressure, overburden and minimum horizontal stresses from standard techniques known in the prior art. The three far-field shear moduli in the three orthogonal planes are obtained from the monitor survey after depletion or injection. Using the acoustoelastic coefficient obtained from the baseline survey and the three shear moduli after depletion or injection, the new algorithm provides estimates of the maximum and minimum horizontal stress magnitudes caused by a change in the reservoir pressure. Estimated maximum and minimum horizontal stresses after depletion or injection together with estimated reservoir pressure can then be used to calculate a safe injection pressure below a threshold to avoid unwanted fractures. They can also be used to provide a safe reservoir pressure window that will reduce chances of any shear slippage at any existing fault.

Estimation of $C_{66}$ Using Borehole Stoneley Dispersion in a Cased Hole

Figure 2:
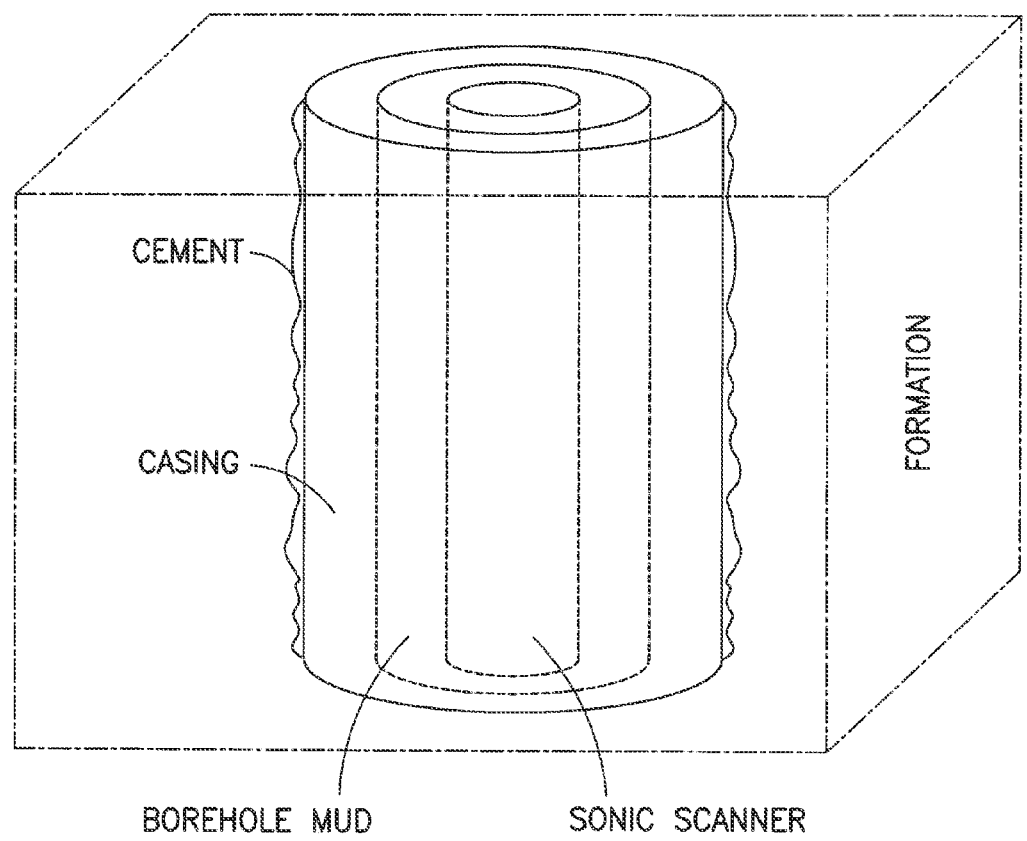
FIG. 2 is a schematic diagram of sonic tool concentrically placed in a cased fluid filled borehole.

FIG. 2 shows a schematic diagram of a sonic tool (yellow solid cylinder) concentrically placed in a fluid-filled cased borehole. The casing is depicted by a hollow brown cylinder. Recorded waveforms at an array of hydrophone receivers can be processed by a modified matrix pencil algorithm to isolate both nondispersive and dispersive arrivals in the wavetrain. The lowest-order, axi-symmetric Stoneley mode is a dispersive mode whose velocity changes as a function of frequency.

The Stoneley dispersion in a fluid-filled borehole in the presence of a casing can also be calculated from the solution of a classical boundary-value problem. The Stoneley dispersion for a borehole surrounded by an effectively isotropic formation can be calculated in the presence of an equivalent tool structure concentrically placed with the borehole axis to account for the tool effects on the measured sonic data. To calculate the Stoneley dispersion in a cased hole surrounded by an effectively isotropic formation, it is necessary to input the following geometrical and material parameters of the equivalent tool structure, borehole fluid, casing material, and formation:

1. Surface impedance condition at the boundary between the tool and borehole fluid;
2. Borehole fluid compressional velocity and mass density;
3. Casing material mass density, compressional and shear velocities;
4. Casing inner and outer diameters; and
5. Formation mass density, compressional and assumed shear velocities.

All of these parameters may be estimated using information that is available from various sources except the formation shear velocity that remains to be estimated for calculating the far-field shear modulus $C_{66}$. Note that the shear modulus estimated from the Stoneley data $C_{66} = \rho V_S^2$, where $V_S$ is the formation shear velocity for an effectively isotropic formation.

Figure 4:
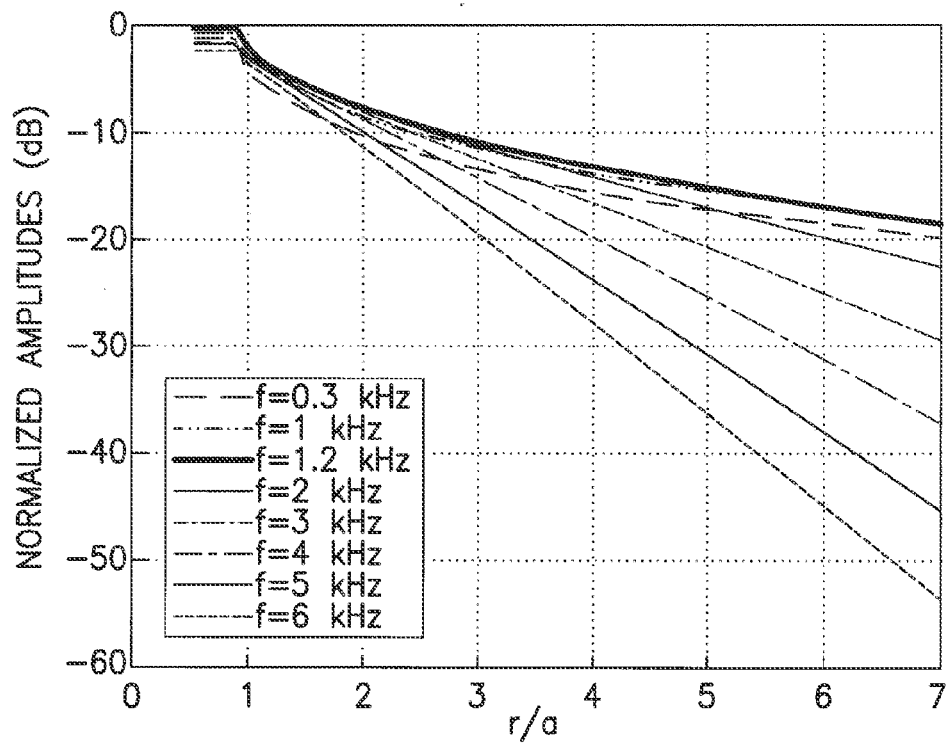
FIG. 4 is a plot of the normalized amplitude as a function of radial variation when the Stoneley mode is varied.

To analyze sonic data in a cased hole, investigating radial depth of investigation as a function of Stoneley wave frequency may be performed. FIGS. 3a and 3b, respectively, show radial variation of displacement and stress amplitudes associated with the Stoneley mode at 3 and 5 kHz. It is clear from these results that Stoneley waves at these frequencies exhibit radial depth of investigation that extends up to about 2× Casing OD (OD: Outer Diameter) in the presence of a well bonded casing. FIG. 4 illustrates radial variations of radial stress $T_{rr}$ as a function of frequency plotted in a logarithmic scale. These results help in selecting a frequency band that probes deepest into the formation. Results from FIG. 4 suggests that the far-field shear modulus must be estimated by minimizing differences between the measured and model predicted Stoneley dispersions over a frequency band of 1 to 3 kHz. Estimation of $C_{66}$ using this frequency band assures a reliable estimate of shear modulus outside any possible near-wellbore alteration.

A technique for the estimation of $C_{66}$ consists of an algorithm that minimizes the difference between the measured and model Stoneley dispersions over a chosen bandwidth where the Stoneley data is mostly sensitive to the far-field formation properties.

The cost function to be minimized can be expressed as $$\varepsilon = \frac{\sum_{i=1}^{N} |S_i^{data} - S_i^{model}|}{\sum_{i=1}^{N} |S_i^{model}|}, \quad (5)$$

where $S_i$ (data) and $S_i$ (model) denote the measured and model predicted Stoneley wave slownesses at different frequencies, and the index $i=1, 2, 3, \ldots N$, denotes chosen slownesses (or velocities) at the i-th frequency.

Figure 5:
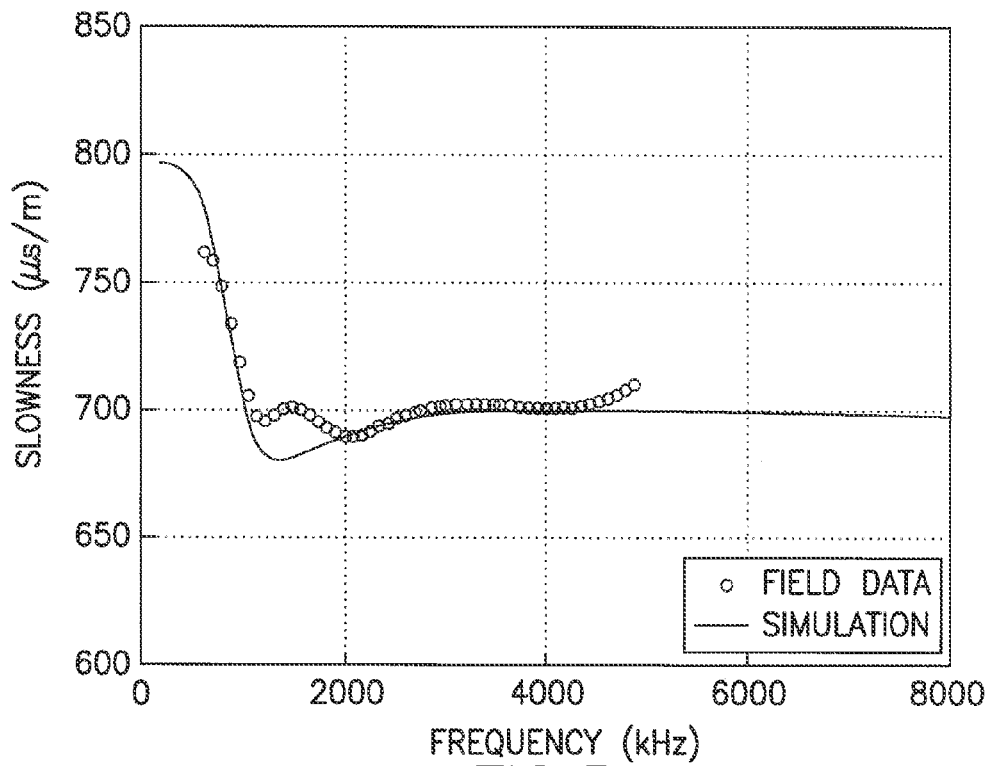
FIG. 5 is a plot of slowness as a function of frequency of the Stoneley mode of field and simulation data.

The value of $C_{66}$ that minimizes the cost function $\epsilon$ as defined in equation (5) is the estimated far-field formation shear modulus. FIG. 5 shows comparison of the measured (blue circles) Stoneley dispersion and model based prediction (solid red curve) obtained with the estimated value of $C_{66}$.

Figure 6A:
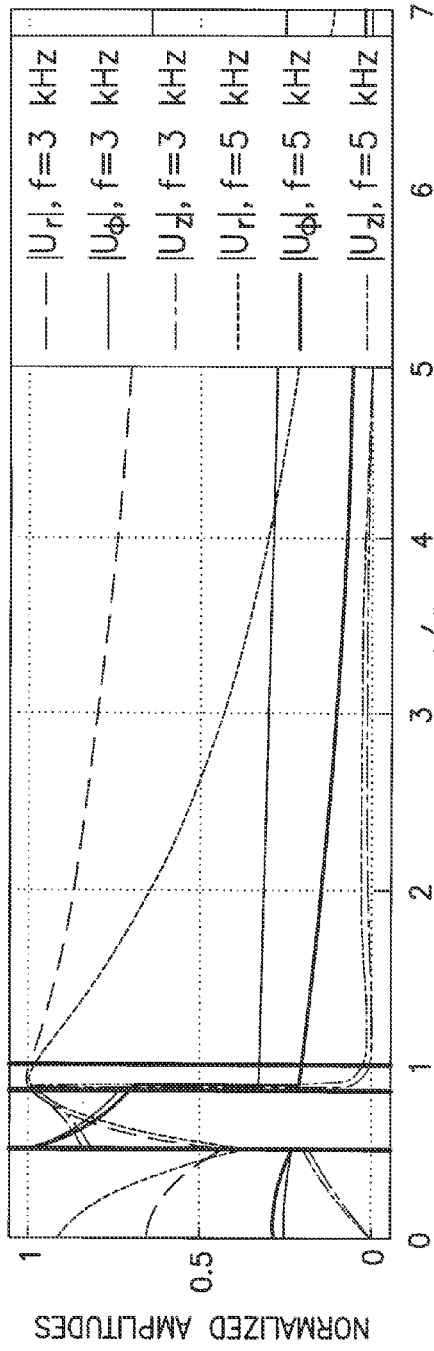
FIG. 6 is a series of plots of the normalized amplitude as a function of radial variation with a dipole mode at 3 and 5 kHZ.
Figure 6B:
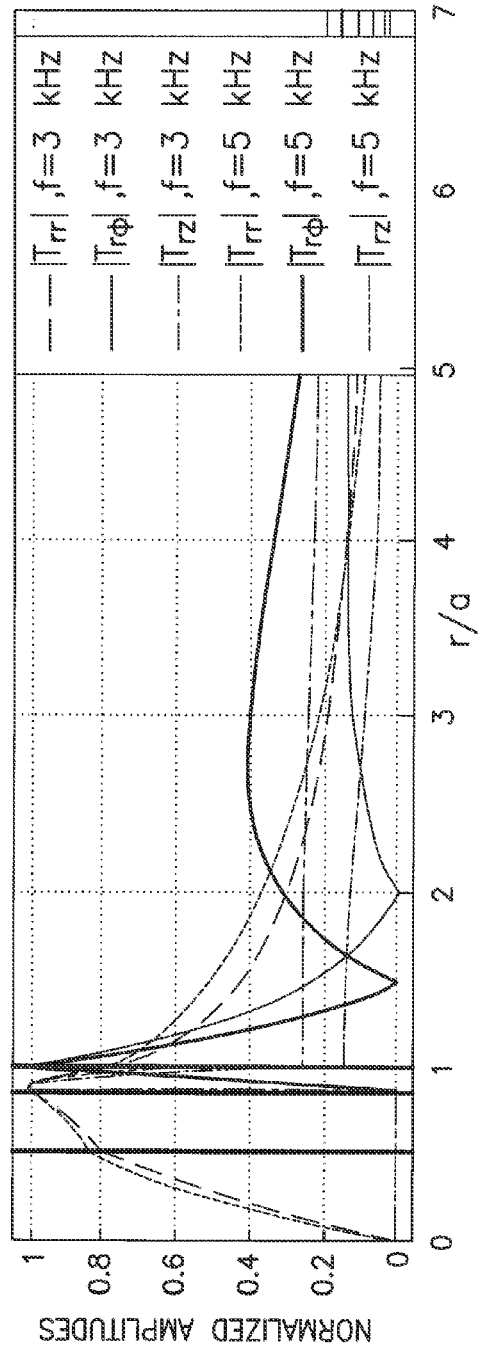

Estimation of $C_{44}$ and $C_{55}$ Using Cross-Dipole Dispersions in a Cased Hole The other two shear moduli $C_{44}$ and $C_{55}$ are obtained from the dipole data acquired in a cased hole. A dipole source placed in a fluid-filled borehole generates refracted headwaves and relatively larger amplitude borehole flexural modes. Processing of an array of recorded waveforms by a modified matrix pencil algorithm yields two flexural dispersions corresponding to the fast and slow shear waves in the orthogonal planes containing the borehole axis. Low-frequency asymptotes of borehole flexural dispersions coincide with the far-field formation shear slownesses. Radial depth of investigation of dipole flexural data as a function of frequency helps in confirming that the estimated shear moduli $C_{44}$ and $C_{55}$ are far-field parameters outside any near-wellbore alteration caused by the cement annulus. FIGS. 6a and 6b, respectively, illustrate radial variations of displacement components and radial stress components as a function of radial distance from the borehole axis normalized by the casing outer radius a. The fast-shear and slow-shear velocities can be readily converted into shear moduli as described by the following equations:

$$C_{44} = \rho V_{SS}^2,$$

$$C_{55} = \rho V_{FS}^2, \quad (6)$$

where $\rho$ is the formation mass density; $V_{SS}$ and $V_{FS}$ are the slow and fast shear velocities obtained from the processing of cross-dipole data. Note that low-frequency asymptotes of flexural dispersions are independent of the presence of casing and any possible sonic tool effects on dipole data.

Thus, we can estimate the three shear moduli using the measured Stoneley and cross-dipole dispersions obtained from sonic waveforms generated by a monopole and two orthogonal dipole transmitters placed in a fluid-filled borehole.

Since it is known that the horizontal shear modulus $C_{66}$ is somewhat reduced in the presence of horizontal fluid mobility in a porous reservoir, this fact can help in putting appropriate bounds on the estimated vertical to horizontal stress ratios. For instance, equations (11a) and (12b) are likely to yield an upper-bound of the estimated vertical to horizontal stress ratio in a reservoir interval where mobility-induced effects on the shear modulus $C_{66}$ are not accounted for. Generally, the tube wave slowness decreases by only about 2 to 3% in the presence of fluid mobility, and this leads to a decrease in $C_{66}$ by about 4 to 6%.

Similarly, it is known that the horizontal shear modulus $C_{66}$ is significantly increased in the presence of high clay content in a shale interval. Consequently, it can be challenging to estimate the ratio of vertical to horizontal stress ratios in shale intervals unless we are able to compensate for the structural anisotropy induced increase in $C_{66}$ from other sources. One way to compensate for the structural anisotropy induced increase in $C_{66}$ is to measure the difference between the shear modulus $C_{66}$ in the bedding plane and $C_{44}$ in a plane perpendicular to the bedding from core samples subjected to a confining pressure at the depth of interest.

Theory

Figure 7:
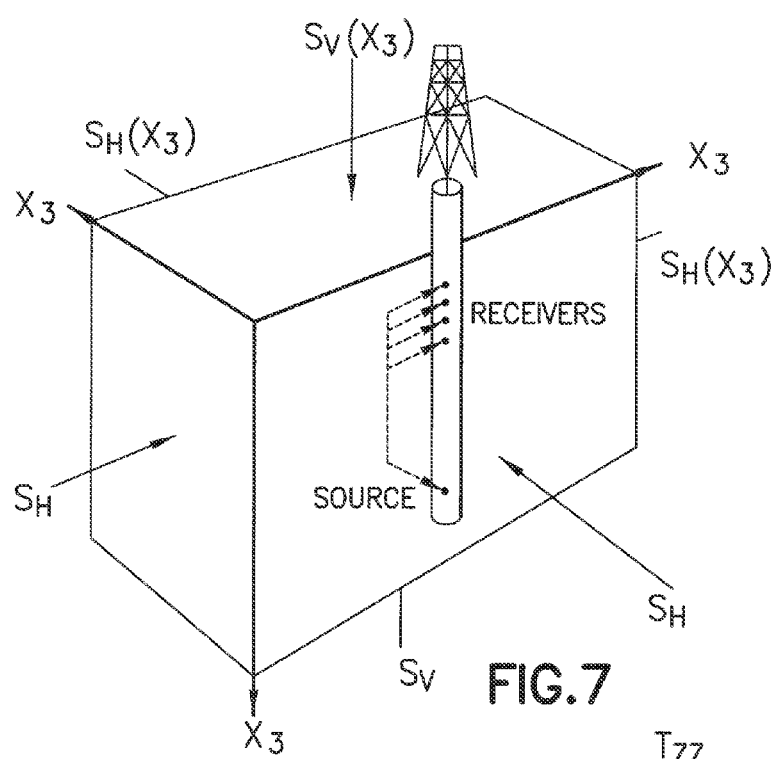
FIG. 7 is a schematic diagram of a borehole in a subterranean formation when two horizontal stresses are equivalent.
Figure 8:
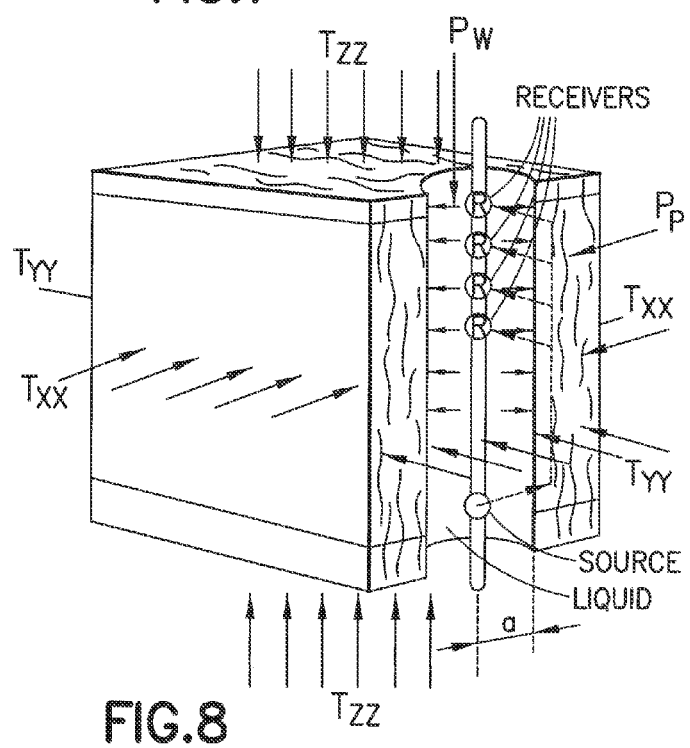
FIG. 8 is a schematic diagram of a borehole in a subterranean formation exposed to multiple stresses and varied pressure.

Consider a borehole parallel to the $X_3$-axis and its cross-sectional plane parallel to the $X_1$-$X_2$-plane as shown in FIG. 7. The overburden stress $S_V$ is parallel to the $X_3$-axis, and the horizontal stress $S_H$ is in the $X_2$-$X_3$ plane. Processing of dipole data acquired by a transmitter aligned with the $X_1$-axis yields the shear modulus $C_{55}$, whereas the other orthogonal transmitter aligned with the $X_2$-axis yields the shear modulus $C_{44}$. The Stoneley data is used to obtain the shear modulus $C_{66}$ in the borehole cross-sectional ($X_1$-$X_2$) plane. Sonic velocities and corresponding elastic moduli are functions of effective stresses in the propagating medium. FIG. 8 shows schematic of a borehole in a triaxially stressed formation where the effective stresses are defined in terms of the total formation stress and pore pressure together with the Biot coefficient $\alpha$. Note that sonic velocities or slownesses are sensitive to effective stresses in the propagating medium. Effective stress $\sigma_{ij} = T_{ij} - \delta_{ij} \alpha P_P$, where $T_{ij}$ is the applied stress, $\delta_{ij}$ is the Kronecker delta, and $\alpha$ is the Biot parameter.

Referred to an isotropically loaded reference state, formation shear moduli in the three orthogonal planes are the same ($C_{44} = C_{55} = C_{66} = \mu$). When this rock is subject to anisotropic incremental stresses, changes in the three shear moduli can be expressed as $$\Delta C_{55} = [C_{55} - \nu C_{144} + (1-\nu)C_{155}]\frac{\Delta\sigma_{11}}{2\mu(1+\nu)} + [C_{144} - \quad (7)$$

$$(1-2\nu)C_{55} - 2\nu C_{155}]\frac{\Delta\sigma_{22}}{2\mu(1+\nu)} +$$

$$[2\mu(1+\nu) + C_{55} - \nu C_{144} + (1-\nu)C_{155}]\frac{\Delta\sigma_{33}}{2\mu(1+\nu)},$$

where $\Delta C_{55}$ is obtained from the fast-dipole shear slowness and formation bulk density, $C_{55}$, Y $[=2\mu(1+\nu)]$, and $\nu$ are the shear modulus, Young's modulus, and Poisson's ratio, respectively; $C_{144}$ and $C_{155}$ are nonlinear constants referred to the chosen reference state; and $\Delta\sigma_{33}$, $\Delta\sigma_{11}$, and $\Delta\sigma_{22}$, respectively, denote changes in the effective overburden, maximum horizontal, and minimum horizontal stresses from an effectively isotropic reference state.

$$\Delta C_{44} = [-(1+2\nu)C_{44} + \nu C_{144} - \quad (8)$$

$$2\nu C_{155}]\frac{\Delta\sigma_{11}}{2\mu(1+\nu)} + [-\nu C_{144} + C_{44} + (1-\nu)C_{155}]\frac{\Delta\sigma_{22}}{2\mu(1+\nu)} +$$

$$[2\mu(1+\nu) + C_{44} - \nu C_{144} + (1-\nu)C_{155}]\frac{\Delta\sigma_{33}}{2\mu(1+\nu)},$$

where $\Delta C_{44}$ is obtained from the slow-dipole shear slowness and formation bulk density at a given depth, and $C_{44}$ ($=C_{55}$) is the shear modulus in the chosen reference state.

$$\Delta C_{66} = [\mu(1+v) + C_{66} - vC_{144} + \quad (9)$$
$$(1-v)C_{155}]\frac{(\Delta\sigma_{11} + \Delta\sigma_{22})}{2\mu(1+v)} + [-(1+2v)C_{66} +$$
$$C_{144} - 2vC_{155}]\frac{\Delta\sigma_{33}}{2\mu(1+v)},$$

where $\Delta C_{66}$ is obtained from the Stoneley shear slowness dispersion and formation bulk density at a given depth, and $C_{66}(=C_{44})$ is the shear modulus in the chosen reference state.

Difference Equations Using the Far-Field Shear Moduli

A reservoir sand in the absence of formation stresses and fluid mobility behaves like an isotropic material characterized by a shear and bulk moduli. However, a complex shaly-sand reservoir is characterized by anisotropic elastic stiffnesses. Anisotropic elastic stiffnesses and the three shear moduli are affected by (a) structural anisotropy; (b) stress-induced anisotropy; and (c) formation mobility. Structural anisotropy caused by clay microlayering in shales is described by transversely-isotropic (TI-) anisotropy that exhibits the horizontal shear modulus $C_{66}$ to be larger than the vertical shear moduli $C_{44}=C_{55}$, in the absence of any stress-induced effects. Shales are impermeable and do not constitute part of a producing reservoir. Since the effect of formation stresses on the effective shear moduli in a sand and shale interval are substantially different, it is necessary to apply appropriate corrections to the measured shear moduli in the estimation of formation stress magnitudes.

The acoustoelastic theory relates changes in the effective shear moduli to incremental changes in the biasing stresses and strains from a reference state of the material. The three shear moduli can be estimated from borehole sonic data. With the recent introduction of algorithms for the Stoneley radial profiling of horizontal shear slowness ($C_{66}$) and dipole radial profiling of vertical shear slownesses ($C_{44}$ and $C_{55}$), we can unambiguously estimate the virgin formation shear moduli. These algorithms account for the sonic tool bias and possible near-wellbore alteration effects on the measured sonic data.

As described above, differences in the effective shear moduli are related to differences in the principal stress magnitudes through an acoustoelastic coefficient defined in terms of formation nonlinear constants referred to a chosen reference state and for a given formation lithology. Next we assume that the $X_1$-, $X_2$-, and $X_3$-axes, respectively, are parallel to the maximum horizontal ($\sigma_H$), minimum horizontal ($\sigma_h$), and vertical ($\sigma_V$) stresses. Under these circumstances, equations (10) yield difference equations in the effective shear moduli in terms of differences in the principal stress magnitudes through an acoustoelastic coefficient defined in terms of formation nonlinear constants referred to a chosen reference state and for a given formation lithology. The following three equations relate changes in the shear moduli to corresponding changes in the effective principal stresses:

$$C_{44} - C_{66} = A_E(\sigma_{33} - \sigma_{11}), \quad (10a)$$

$$C_{55} - C_{66} = A_E(\sigma_{33} - \sigma_{22}), \quad (10b)$$

$$C_{55} - C_{44} = A_E(\sigma_{11} - \sigma_{22}), \quad (10c)$$

where $\sigma_{33}$, $\sigma_{11}$, and $\sigma_{22}$ denote the effective overburden, maximum horizontal, and minimum horizontal stresses, respectively; and $$A_E = 2 + \frac{c_{456}}{\mu}, \quad (11a)$$

is the acoustoelastic coefficient, $C_{55}$ and $C_{44}$ denote the shear moduli for the fast and slow shear waves, respectively; $C_{456}=(C_{155}-C_{144})/2$, is a formation nonlinear parameter that defines the acoustoelastic coefficient; and $\mu$ represents the shear modulus in a chosen reference state. However, only two of the three difference equations in (10) are independent.

The presence of unbalanced stress in the cross-sectional plane of borehole causes dipole shear wave splitting and the observed shear slowness anisotropy can be used to calculate the acoustoelastic coefficient $A_E$ from equation (10c) provided we have estimates of the two principal stresses ($\sigma_{11}$ and $\sigma_{22}$) as a function of depth. Note that the dipole shear waves are largely unaffected by the fluid mobility. We can then estimate the stress-induced change in the Stoneley shear modulus $C_{66}$ using equations (10a) and (10b), and the effective stress magnitudes $\sigma_V$, $\sigma_H$, and $\sigma_h$ at a given depth.

When we have estimates of the minimum horizontal ($\sigma_{22}$) and overburden ($\sigma_{33}$) stress magnitudes as a function of depth, we can determine the acoustoelastic parameter $A_E$ in terms of the far-field shear moduli $C_{55}$ and $C_{66}$ using the relation $$A_E = \frac{c_{55} - c_{66}}{\sigma_V - \sigma_h}, \quad (11b)$$

where we assume that the effects of permeability on these shear moduli are essentially similar and negligible.

Once we have determined the acoustoelastic parameter for a given lithology interval, we can determine the maximum horizontal stress $\Delta S_H$ magnitude as a function of depth from the following equation $$\sigma_H = \sigma_h + \frac{c_{55} - c_{44}}{A_E}, \quad (12a)$$

where $C_{55}$ and $C_{44}$ denote the fast and slow dipole shear moduli, respectively. Similarly, the minimum horizontal stress $S_h$ magnitude as a function of depth from the following equation $$\sigma_h = \sigma_V - \frac{c_{55} - c_{66}}{A_E}, \quad (12b)$$

Hence, we can estimate formation horizontal stress magnitudes as a function of depth in terms of the three shear moduli $C_{44}$, $C_{55}$, and $C_{66}$, and the acoustoelastic coefficient $A_E$.

Estimation of the Maximum Horizontal Stress Magnitude

Differences in the three shear moduli outside the stress concentration annulus are related to differences in the three principal stresses in terms of an acoustoelastic coefficient referred to a local reference state. There are two independent difference equations that relate the effective overburden, maximum and minimum horizontal stress magnitudes and the acoustoelastic coefficient. These two equations can be solved for the maximum horizontal stress magnitude and acoustoelastic coefficient provided the overburden and minimum horizontal stress magnitudes are known from other sources.

The overburden stress is reliably known from the formation bulk density. The minimum horizontal stress can be reliably estimated from either a mini-frac test or leak-off test and interpolated over a reasonably uniform lithology. Therefore, we can use equation (12a) to calculate the maximum horizontal stress magnitude at a given depth that exhibits dipole dispersion crossover as an indicator of stress-induced shear slowness anisotropy dominating the data.

Estimation of Stress Magnitudes in TI-Shale

To estimate stress magnitudes in TI-shale using the three shear moduli, it is necessary to compensate for the structural anisotropy effects on the difference between the Stoneley shear modulus $C_{66}$ and dipole shear modulus $C_{44}$ or $C_{55}$. Generally, shear modulus $C_{66}$ in the isotropic plane of a TI-shale is larger than shear modulus $C_{44}$ or $C_{55}$ in the sagittal planes ($X_2$-$X_4$ or $X_3$-$X_1$ planes). When we have an independent estimate of TI-anisotropy from core data under confining pressure, we can express structural anisotropy induced increase in $C_{66}$ in terms of the Thomsen parameter $\gamma$. The ratio of $C_{66}/C_{44}$ can be expressed as $$\frac{C_{66}}{C_{44}} = 1 + 2\gamma. \tag{13}$$

If $\gamma=0.2$, the ratio $C_{66}/C_{44}=1.4$. Under this situation, we need to reduce the measured $C_{66}$ by 40 percent before inputting the shear modulus $C_{66}$ together with the shear moduli $C_{44}$ and $C_{55}$ into the stress magnitude estimation algorithm using the three shear moduli algorithm. Here we assume that any remaining differences between $C_{44}$, $C_{55}$, and $C_{66}$ are solely caused by differences in the three principal stresses.

When the Thomsen parameter $\gamma$ is not known, we suggest that we run the stress magnitude estimation algorithm for a range of $C_{66}$ that covers possible influence of TI-anisotropy effects. We can then plot stress magnitudes as a function of parameter $C_{66}'/C_{66}$, where $C_{66}$ is the measured Stoneley shear modulus at a chosen depth, and $C_{66}'$ is the modified shear modulus in a shale interval where $C_{66}'<C_{66}$.

Reservoir Stresses after Depletion or Injection

Consider a vertical fluid-filled borehole parallel to the $X_3$-direction, and the maximum and minimum horizontal stresses parallel to the $X_1$- and $X_2$-directions, respectively.

Sonic data acquired in a fluid-filled open or cased hole can be inverted to obtain the three far-field formation shear moduli. These three shear moduli together with the effective overburden and minimum horizontal stresses in a baseline survey provide an estimate of the maximum horizontal stress magnitude together with an acoustoelastic coefficient as given by the following equations:

$$A_E = \frac{C_{55}^B - C_{66}^B}{\sigma_V^B - \sigma_h^B}, \tag{14}$$

$$\sigma_H^B = \sigma_h^B + \frac{(C_{55}^B - C_{44}^B)}{A_E} \tag{15}$$

where the superscript "B" denotes quantity before depletion or injection, and the effective stress $\sigma_{ij}$ is given by $$\sigma_{ij} = S_{ij} - \alpha \delta_{ij} P_P, \tag{16}$$

where $S_{ij}$ is the total stress, $\delta ij$ is the Kronecker delta, $\alpha$ is the Biot coefficient, and $P_P$ is the pore or reservoir pressure. The total overburden stress is estimated by integrating the bulk density from the surface to the depth of interest and the minimum horizontal stress is estimated by a mini-frac or extended leak-off tests.

The difference between the effective overburden and minimum horizontal stress after depletion and injection can be described by $$\sigma_V^A - \sigma_h^A = \frac{(C_{55}^A - C_{66}^A)}{A_E}, \tag{17}$$

where the superscript "A" denotes quantity after depletion or injection, and it is assumed that the overburden stress is essentially the same as before depletion and injection. When the depletion of the reservoir is rather extensive that there is no bridging effect, the total vertical stress will be carried by the formation and the total vertical stress will be essentially the same as before.

The total minimum and maximum horizontal stresses after depletion can then be given by the following equations $$S_h^A = S_V^B - (\sigma_V^A - \sigma_h^A), \tag{18}$$

$$S_H^A = S_V^B - (\sigma_V^A - \sigma_H^A), \tag{19}$$

where $S_h^A$ and $S_H^A$ denote the total minimum and maximum horizontal stresses in the reservoir after depletion or injection.

Stress Magnitude Estimation in Permeable Reservoirs

Stress magnitude estimation algorithms assume that the observed differences in the three shear moduli are caused by differences in the three formation principal stresses.

However, when fluid permeability and stress-induced effects are simultaneously present on the measured effective shear moduli in a permeable reservoir, it is necessary to remove mobility-induced bias from the stress magnitude estimation workflow. The presence of fluid mobility causes a decrease in the Stoneley shear modulus $C_{66}$ that can be estimated when fluid mobility/permeability is known from an independence source, such as core data or NMR. Under this situation, we modify the measured Stoneley shear modulus $C_{66}$ and input the modified $C_{66}'$ ($>C_{66}$) into the stress magnitude estimation algorithm.

Otherwise, the formation overburden to horizontal stress ratio can be obtained as a function of parameter $\gamma=C'_{66}/C_{66}$ ($>1$). Generally, this parameter $\gamma$ can vary from 1 to 1.15.

Stress Magnitude Estimation in TI-Shales

Recall that stress magnitude estimation algorithms assume that differences in the three shear moduli are solely caused by differences in the three principal stresses.

However, transversely-isotropic shales in the absence of stresses exhibit larger shear modulus $C_{66}$ in the isotropic plane than the shear moduli $C_{44}$ and $C_{55}$ in the two orthogonal sagittal planes.

Therefore, it is necessary to remove any differences between $C_{66}$ and $C_{44}$ caused by structural anisotropy and invert any remaining differences in shear moduli for formation stress magnitudes.

Illustrative Example I

Figure 9:
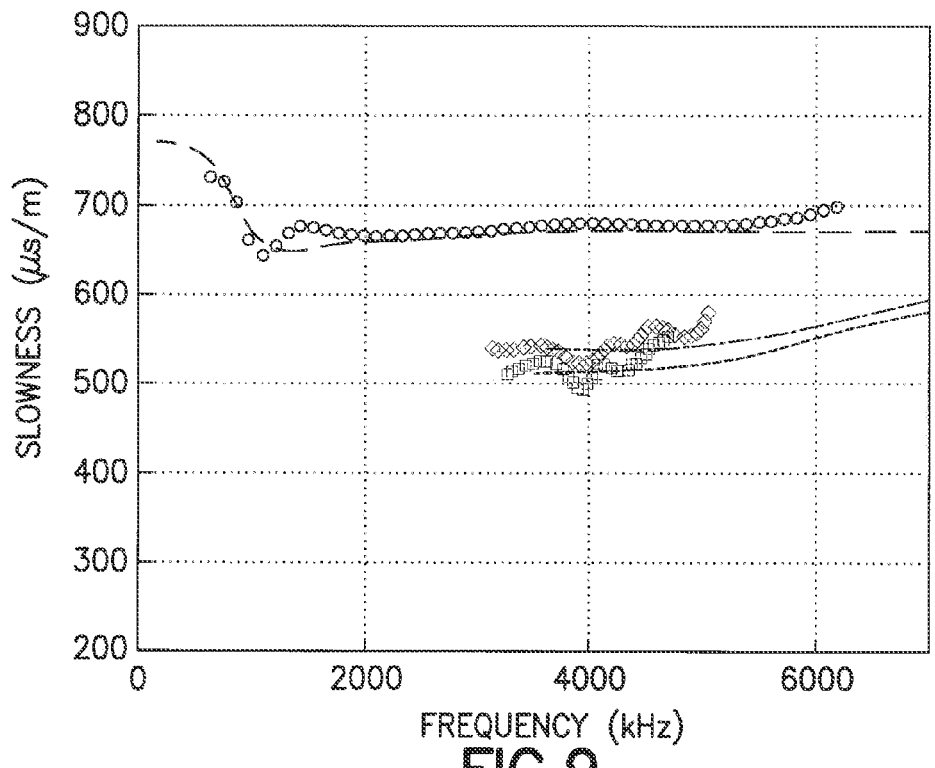
FIG. 9 is plot of slowness as a function of frequency for a borehole in an initial state.
Figure 10:
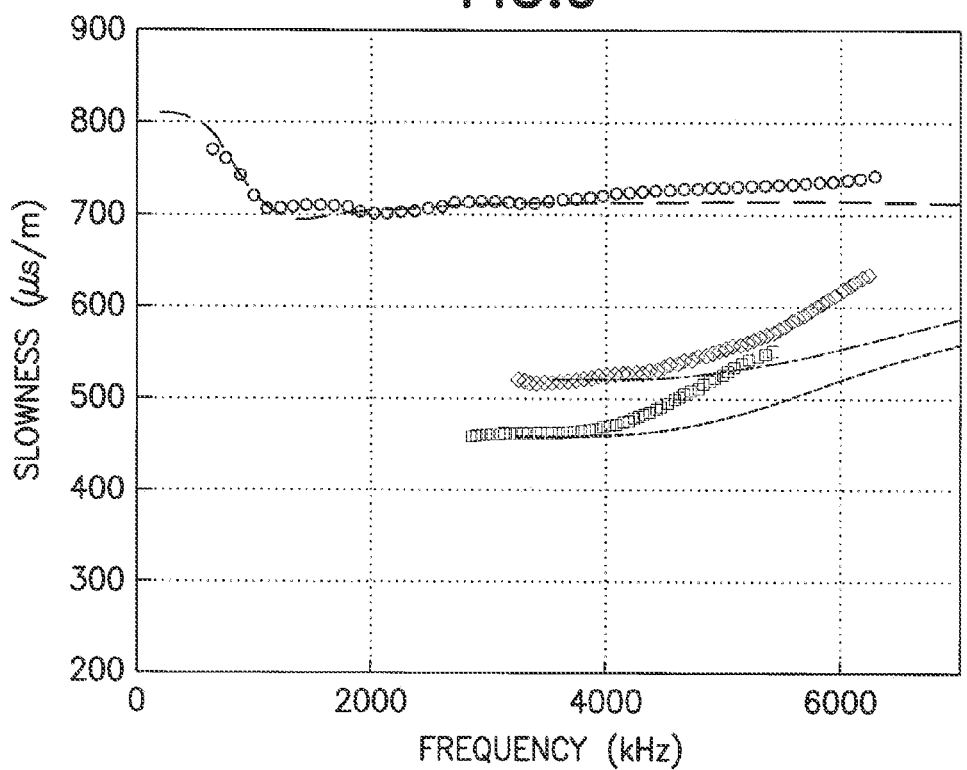
FIG. 10 is a plot of slowness as a function of frequency for a borehole in a borehole survey after injection for observed and simulation results.

Consider a baseline survey at a given depth A in a depleted reservoir that consists of measured Stoneley (blue circles) and cross-dipole dispersions as shown in FIG. 9. The green and cyan circles denote the fast and slow dipole dispersions. The dashed lines are model based theoretical dispersions that account for the presence of a tool structure and well bonded casing. The three theoretical curves yield estimated shear moduli $C_{66}$, $C_{55}$, and $C_{44}$ at the chosen depth before any fluid injection. FIG. 10 shows measured Stoneley and cross-dipole dispersions at the same depth AFTER the field was subjected to fluid injection for about a year. The notation is the same as in FIG. 9. Differences between borehole dispersions in FIGS. 9 and 10 are caused by changes in the reservoir pressure and effective horizontal stresses.

Figure 11:
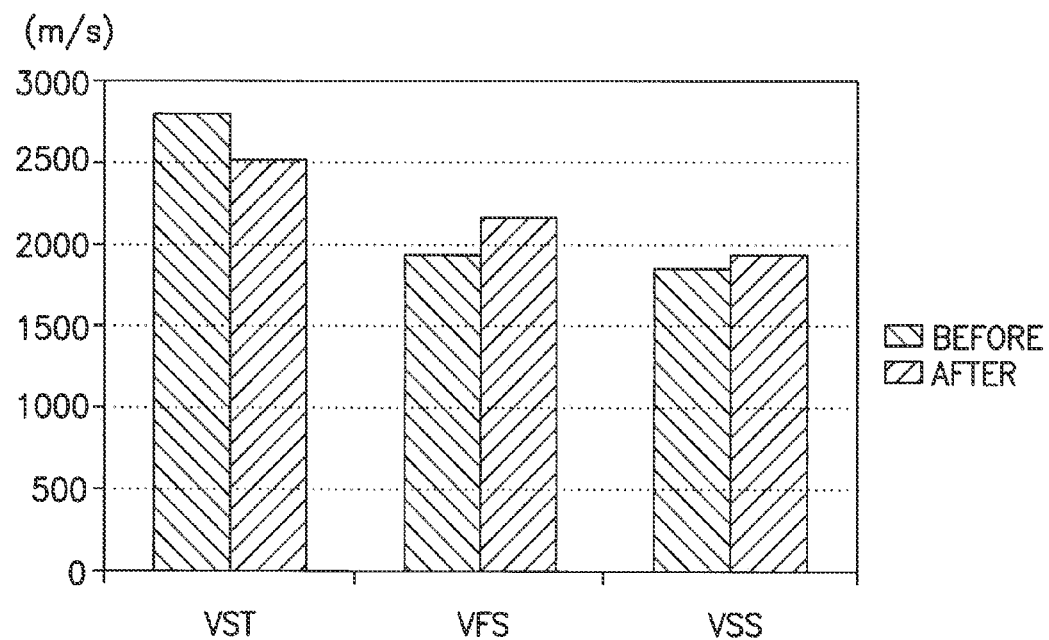
FIG. 11 is a plot of shear velocity as a function of before and after injection.
Figure 12:
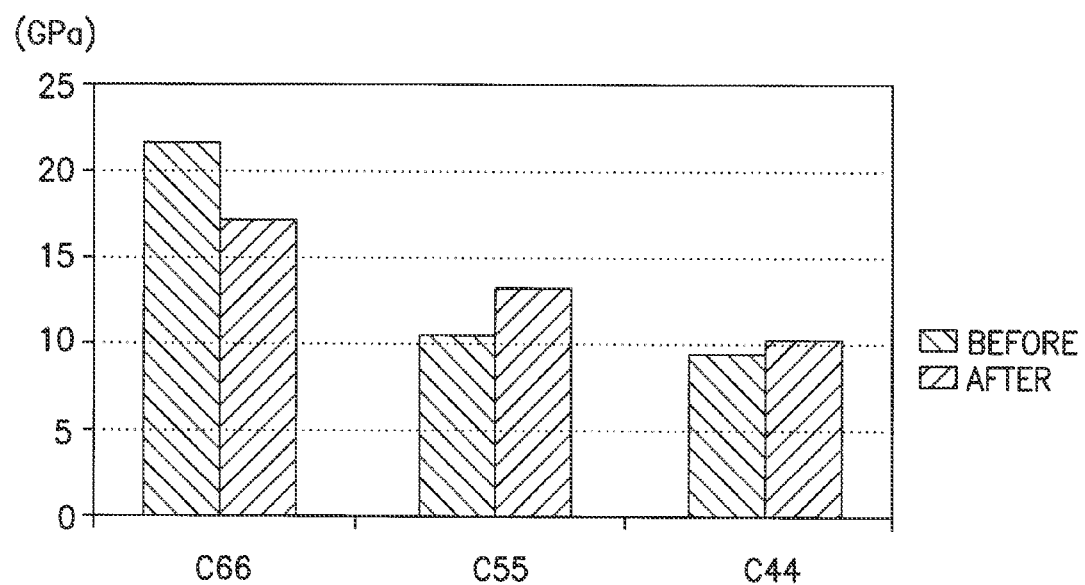
FIG. 12 is a plot of shear moduli as a function of before and after injection.

FIG. 11 illustrates measured changes in the Stoneley shear, fast-dipole shear, and slow-dipole shear velocities before and after fluid injection. The corresponding changes in the shear moduli $C_{66}$, $C_{55}$, and $C_{44}$ are shown in FIG. 12.

Figure 13:
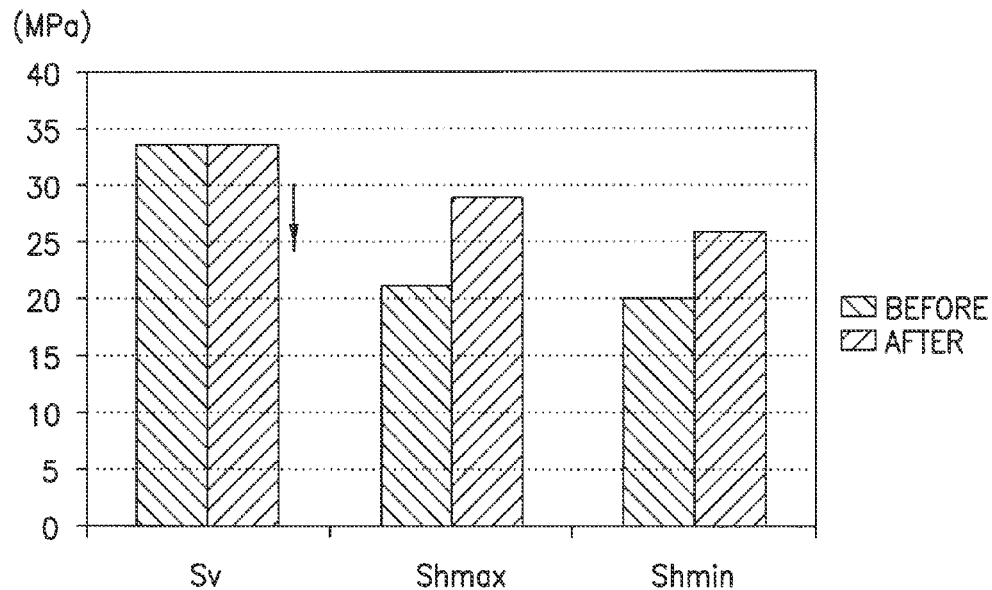
FIG. 13 is a plot of estimated stress changes as a function of before and after injection.

We invert these changes in measured shear moduli caused by fluid injection to estimate corresponding changes in the reservoir stresses. These changes in the maximum and minimum horizontal stresses are illustrated in FIG. 13.

Figure 14:
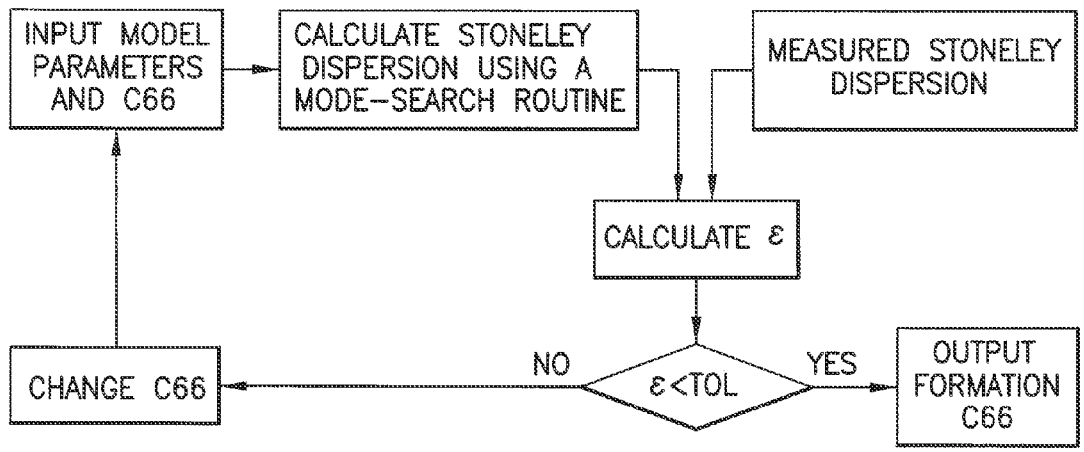
FIG. 14 is a flow chart for the estimation of formation shear modulus using Stoneley data in a cased hole.

FIG. 14 shows a flow chart that highlights various steps in the estimation of $C_{66}$ by minimizing differences between measured and model predicted Stoneley dispersions over a chosen bandwidth. The calculated Stoneley dispersion accounts for the sonic tool effects in the mode-search routine. Differences between the measured and model predicted dispersions ($\epsilon$) are minimized to an acceptable tolerance "Tol" in the iteration process.

Figure 15:
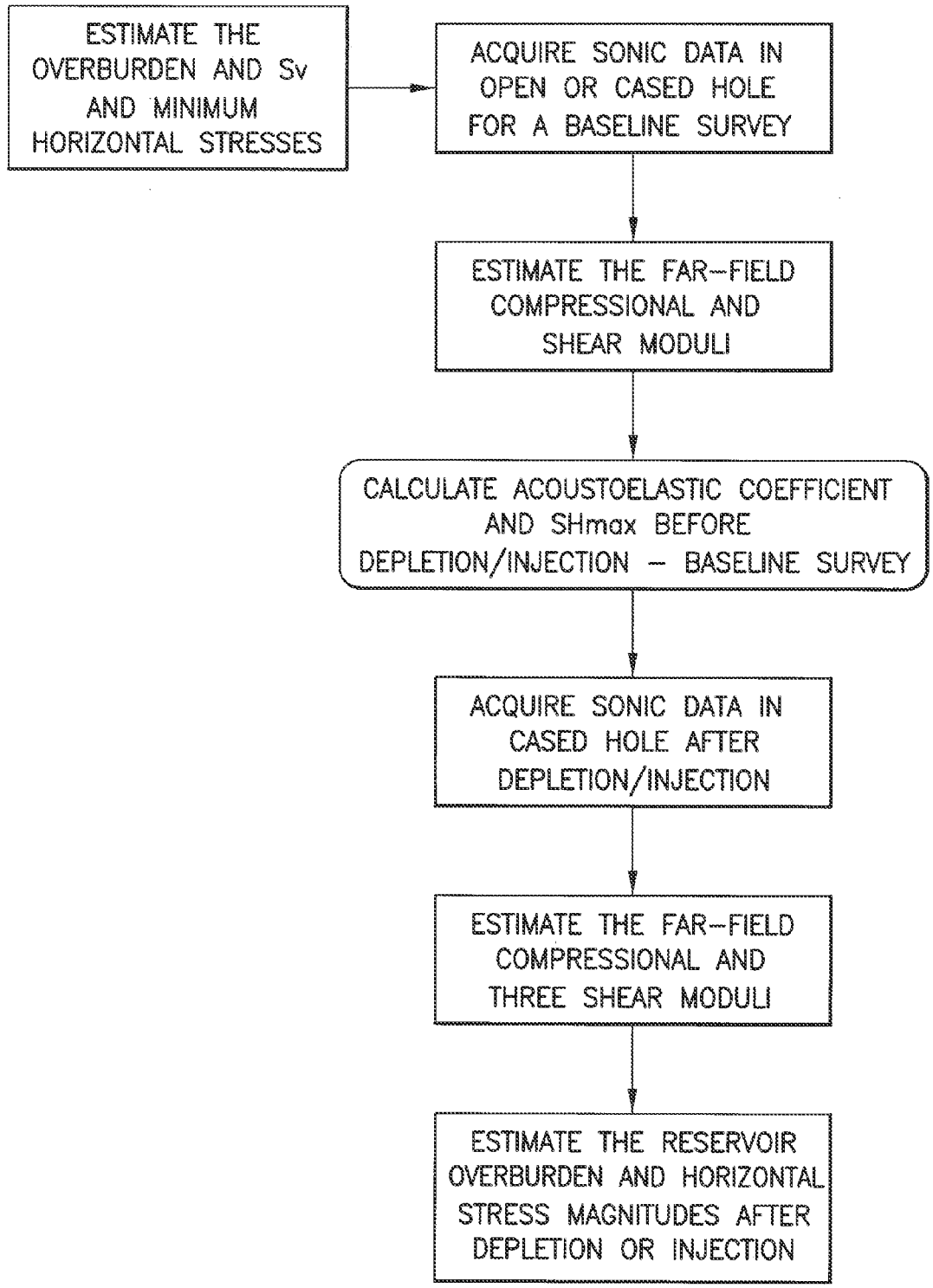
FIG. 15 is a flow chart for the estimation of reservoir stresses using time lapse sonic data acquired before and after reservoir depletion or injection.

FIG. 15 illustrates the various steps necessary for this procedure. FIG. 15 is a flow chart for the estimation of reservoir stresses using time-lapse sonic data acquired before and after reservoir depletion or injection. The algorithm assumes that the reservoir pressure, overburden and minimum horizontal stresses are known in a baseline survey before any depletion or injection.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, where as a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words "means for" together with an associated function.

The invention claimed is:

1. A method for monitoring reservoir stresses in a subterranean formation, the method comprising:
   collecting baseline sonic data for the formation using a sonic logging tool before a project on the formation is performed;
   collecting subsequent sonic data for the formation using a sonic logging tool after collecting the baseline sonic data and after the project on the formation has been performed, wherein the project comprises at least one of (i) recovering hydrocarbons from the formation and (ii) injecting fluid into the formation;
   calculating Stoneley and cross dipole dispersions using the baseline sonic data and subsequent sonic data;
   estimating changes in minimum and maximum horizontal stress magnitudes in the formation for the project using the calculated dispersions; and
   determining a pressure for maintaining integrity of the formation using the changes in minimum and maximum horizontal stress magnitudes.

2. The method of claim 1, wherein the subsequent sonic data is collected in an open borehole.

3. The method of claim 1, wherein the subsequent sonic data is collected in a cased borehole.

4. The method of claim 1, wherein the baseline sonic data comprises estimates of reservoir pressure, overburden, and minimum horizontal stresses.

5. The method of claim 1, wherein the baseline sonic data and subsequent sonic data are collected in a borehole.

6. The method of claim 5, further comprising inverting the Stoneley dispersion to estimate far field shear modulus $C_{66}$ in a cross sectional plane of the borehole.

7. The method of claim 6, further comprising using low frequency asymptotes of two flexural dispersions to calculate two shear dispersions $C_{44}$ and $C_{55}$.

8. The method of claim 1, wherein the project comprises recovering hydrocarbons.

9. The method of claim 1, wherein the project comprises injecting a fluid into the formation.

10. The method of claim 9, wherein the project comprises injecting a gas into the formation.

11. The method of claim 1, wherein the pressure for maintaining integrity of the formation comprises an injection pressure for fluid injection into the formation.

12. The method of claim 1, wherein the pressure for maintaining integrity of the formation comprises a reservoir pressure.

13. The method of claim 12, wherein the reservoir pressure comprises a reservoir pressure window at which to maintain the formation.

14. The method of claim 13, wherein the reservoir pressure window comprises a reservoir pressure window at which to maintain the formation during depletion of the formation.

15. A method for monitoring reservoir stresses in a subterranean formation, the method comprising:
   collecting baseline sonic data in a borehole traversing the formation using a sonic logging tool;
   collecting subsequent sonic data in the borehole using a sonic logging tool after collecting baseline sonic data and after recovering hydrocarbons from the formation;
   calculating Stoneley and cross dipole dispersions using the baseline sonic data and subsequent sonic data;
   estimating (i) maximum and minimum horizontal stresses in the formation before recovering hydrocarbons and (ii) maximum and minimum horizontal stresses in the formation after recovering hydrocarbons using the calculated dispersions; and
   determining a pressure for maintaining integrity of the formation using (i) the maximum and minimum horizontal stresses in the formation before recovering hydrocarbons and (ii) the maximum and minimum horizontal stresses in the formation after recovering hydrocarbons.

16. The method of claim 15, wherein the baseline sonic data comprises estimates of reservoir pressure, overburden, and minimum horizontal stresses.

17. The method of claim 15, further comprising inverting the Stoneley dispersion to estimate far field shear modulus $C_{66}$ in a cross sectional plane of the borehole.

18. The method of claim 17, further comprising using low frequency asymptotes of two flexural dispersions to calculate two shear dispersions $C_{44}$ and $C_{55}$.

19. The method of claim 15, wherein the pressure for maintaining integrity of the formation comprises an injection pressure for fluid injection into the formation.

20. The method of claim 15, wherein the pressure for maintaining integrity of the formation comprises a reservoir pressure.

21. The method of claim 20, wherein the reservoir pressure comprises a reservoir pressure window at which to maintain the formation.

22. The method of claim 21, wherein the reservoir pressure window comprises a reservoir pressure window at which to maintain the formation during depletion of the formation.

* * * * *